United States Patent [19]

Daniel et al.

[11] 4,328,244
[45] May 4, 1982

[54] NOVEL (((SUBSTITUTED-PHENYL)METHYL-)AMINO)BENZENESULFONIC ACIDS AND PHARMACEUTICALLY-ACCEPTABLE SALTS THEREOF

[75] Inventors: John K. Daniel; Donald P. Matthews; Norton P. Peet, all of Indianapolis, Ind.

[73] Assignee: The Dow Chemical Company, Midland, Mich.

[21] Appl. No.: 152,076

[22] Filed: May 21, 1980

[51] Int. Cl.³ ............... A61K 31/275; A61K 31/185; C07C 143/58; C07C 121/50
[52] U.S. Cl. ..................... 424/304; 260/465 E; 260/508; 260/509; 260/510; 424/315
[58] Field of Search ........... 260/508, 509, 510, 465 E; 424/304, 315

[56] References Cited

U.S. PATENT DOCUMENTS

| | | | |
|---|---|---|---|
| 622,854 | 4/1899 | Homolka et al. | 260/508 |
| 640,563 | 1/1900 | Homolka et al. | 260/508 |
| 648,261 | 4/1900 | Homolka et al. | 260/508 |
| 726,688 | 4/1903 | Homolka et al. | 260/508 |

OTHER PUBLICATIONS

Badische, Chem. Abstract, 55, 26460e (1960) (Abstract of German Pat. No. 1,076,079).
Borecky, J. Chromatography, 9, 472 (1962).
Borodkin, J. Appl. Chem., USSR, pp. 741–743 (1955).

Primary Examiner—Nicky Chan

[57] ABSTRACT

Novel (((substituted-phenyl)methyl)amino)benzenesulfonic acids having antiviral activity are disclosed. Compounds within the scope of the invention have the formula

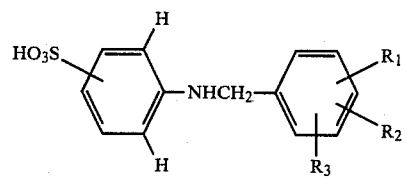

wherein $R_1$ represents lower alkyl, lower alkoxy, nitro, amino, cyano, trifluoromethyl, acetyl, methylthio, methylsulfinyl, methylsulfonyl, benzoyl, substituted benzoyl, aminosulfonyl or halogen; and $R_2$ and $R_3$ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl, aminosulfonyl or halogen. The invention also includes the pharmaceutically-acceptable salts of the novel (((substituted-phenyl)methyl)amino)benzenesulfonic acids. Methods of using the compounds as antiviral agents are also disclosed, as well as compositions which comprise a carrier in combination with a suitable antiviral active compound.

18 Claims, No Drawings

NOVEL (((SUBSTITUTED-PHENYL)METHYL)AMINO)-BENZENESULFONIC ACIDS AND PHARMACEUTICALLY-ACCEPTABLE SALTS THEREOF

SUMMARY OF THE INVENTION

The present invention is directed to a compound of the formula:

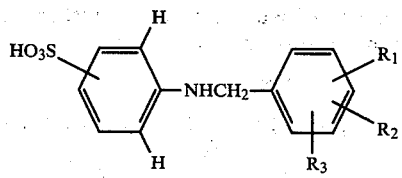

wherein $R_1$ represents lower alkyl, lower alkoxy, nitro, amino, cyano, trifluoromethyl, acetyl, methylthio, methylsulfinyl, methylsulfonyl, benzoyl, substituted benzoyl, aminosulfonyl or halogen; and $R_2$ and $R_3$ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl, aminosulfonyl or halogen. The invention also includes the pharmaceutically-acceptable salts of the compounds described herein.

As used herein, the term "halogen" represents bromo, chloro or fluoro; "lower alkyl" refers to an alkyl group having from 1 to 3 carbon atoms, such as methyl, ethyl, propyl or isopropyl; "lower alkoxy" refers to an alkoxy group having from 1 to 3 carbon atoms such as methoxy, ethoxy, propoxy or isopropoxy; "substituted benzoyl" refers to a benzoyl group in which the benzene ring is monosubstituted, disubstituted or trisubstituted with substituents selected from the group consisting of bromo, chloro or methyl; and "pharmaceutically-acceptable salts" refers to the acid addition salts of those bases which will form a salt with the benzenesulfonic acid and which will not cause an adverse physiological effect when administered to an animal at dosages consistent with good pharmacological activity. Suitable bases thus include the alkali metal and alkaline earth metal hydroxides, carbonates and bicarbonates, such as sodium hydroxide, potassium hydroxide, calcium hydroxide, potassium carbonate, sodium bicarbonate and magnesium carbonate.

In general, the compounds within the scope of the invention are solids having some water solubility and varying solubility in organic solvents such as methylene chloride, methanol and ethanol. The compounds disclosed herein exhibit antiviral activity and thus can be used to inhibit viral replication by contacting a virus and, preferably, virus host cells with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 0.00001 percent (%) or less to about 99% by weight of the active compound in combination with a pharmaceutically-acceptable carrier. Typically, in those compositions employing a low percentage of active compound, the pharmaceutically-acceptable carrier is in liquid form, therefore a composition containing 0.00001% or less by weight of active compound is equivalent to a composition containing about 0.1 microgram (μg) or less of the active compound per milliliter (ml) of carrier.

DETAILED DESCRIPTION OF THE INVENTION

Compounds within the scope of the present invention are prepared by reacting a compound of the formula:

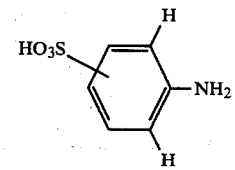

(sulfanilic acid, i.e. 4-aminobenzenesulfonic acid, when the desired subject compound is a 4-(((substituted-phenyl)methyl)amino)benzenesulfonic acid derivative or metanilic acid, i.e. 3-aminobenzenesulfonic acid when a 3-(((substituted-phenyl)methyl)amino)benzenesulfonic acid derivative is desired) with a ring substituted benzyl halide of the formula:

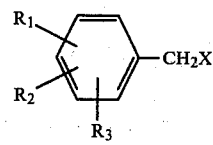

wherein X represents halide, generally bromide or chloride; and $R_1$, $R_2$ and $R_3$ have the same meanings as previously defined herein.

The reaction proceeds when the above reactants (preferably, in approximately equimolar concentrations) are contacted and mixed in water, and heated to a temperature, generally from about 40° C. to about 90° C. in the presence of a base, such as sodium hydroxide, for a time sufficient to obtain the desired subject compound as a salt, usually from about 3 hours to about 8 hours, although longer reaction times may be required.

The free acid is obtained by treating the salt with an appropriate acid, such as hydrochloric acid. The salt of free acid is recovered from the reaction mixture by conventional procedures such as filtration, centrifugation and decantation. Purification of the product is accomplished by procedures well known in the art, such as recrystallization.

Alternatively, compounds within the scope of the invention can be prepared by adding the preselected ring-substituted benzyl halide (usually, as a solution of the benzyl halide in acetonitrile) to a mixture of the compound of formula II (i.e., sulfanilic acid or metanilic acid) in water and acetonitrile in the presence of a base such as sodium acetate or sodium acetate trihydrate. The resulting mixture is refluxed for a time sufficient to obtain the desired subject compound as a salt. Usually a reflux time of about 2 to about 7 hrs. is sufficient. The free acid can be obtained and recovered as previously described herein.

The following examples are included to further illustrate the invention but are not to be construed as a limitation thereon.

EXAMPLE 1

Sodium 4-(((3-Chlorophenyl)methyl)amino)benzenesulfonate

A mixture of 17.2 g of sulfanilic acid, 100 ml of 5 Normal (N) sodium hydroxide solution, 100 ml of water and 16.1 g of 3-chlorobenzyl chloride was stirred in a 500-ml Erlenmeyer flask and heated to about 40°–50° C. After 5 days, a small portion of the reaction mixture was poured into dilute hydrochloric acid. A white precipitate formed which was insoluble in boiling water. The remaining portion of the reaction mixture was poured over 800 ml of ice-water, acidified with concentrated hydrochloric acid, and then filtered through a sintered glass funnel. After filtering, about 50 ml of slurry remained in the funnel. This slurry was put in a beaker, 200 ml of ethanol was added and the mixture was warmed to about 50° C. A solution of 5N sodium hydroxide was added dropwise until solution was achieved. The solution was carbon treated and filtered. Concentration of the filtrate gave a gummy semisolid which was recrystallized from 200 ml of acetic acid containing a small quantity of water. After vacuum oven drying, 5.4 g of the purified product, sodium 4-(((3-chlorophenyl)methyl)amino)benzenesulfonate, was obtained as an off-white solid having a melting point (mp) greater than 280° C.

A nuclear magnetic resonance spectrum confirmed the structure.

EXAMPLE 2

Sodium 4-(((4-Fluorophenyl)methyl)amino)benzenesulfonate

To 17.3 g (0.1 mole) of sulfanilic acid, 100 ml of 5N sodium hydroxide solution and 100 ml of water was added 14.4 g (0.1 mole) of 4-fluorobenzyl chloride which was then mixed and heated to about 45°–55° C. in a 500-ml Erlenmeyer flask for 48 hours. After heating, the reaction mixture was poured over approximately 1 liter of cold water and acidified with concentrated hydrochloric acid. The resulting slurry was slowly filtered through a fine sintered glass funnel and a top clear yellow solution which did not pass through the filter was decanted away and discarded. The remaining off-white solid was mixed with 100 ml of ethanol and aqueous NaOH solution was added slowly until solution was achieved. The solution was then carbon treated, filtered and concentrated under reduced pressure to obtain 9.0 g of the crude product. Recrystallization from 80 ml of glacial acetic acid, followed by vacuum oven drying gave 2.4 g of the purified product, sodium 4-(((4-fluorophenyl)methyl)amino)benzenesulfonate, as white crystals which decomposed at 275° C.

The structure was confirmed by nuclear magnetic resonance spectroscopy.

EXAMPLE 3

Sodium 4-(((3,4-Dimethylphenyl)methyl)amino)benzenesulfonate

To 17.3 g of sulfanilic acid, 100 ml of 5N sodium hydroxide solution and 100 ml of water was added 15.5 g of 3,4-dimethylbenzyl chloride and the resulting mixture was then heated to about 50°–60° C. in a 500-ml Erlenmeyer flask for 72 hours. The reaction mixture was poured over approximately 1 liter of ice-water and acidified with concentrated hydrochloric acid to give a solid. The solid was collected by filtration and washed with 100 ml of diethyl ether. Then the product was slurried in hot water and filtered again. After drying, 6.4 g of solid was obtained. The solid was slurried in ethanol and one equivalent of an aqueous sodium hydroxide solution added. Upon removal of the solvent under reduced pressure, 8.2 g of a tan semi-solid was obtained. Recrystallization from an ethanol/water solution gave 1.4 grams of the purified product, sodium 4-(((3,4-dimethylphenyl)methyl)amino)benzenesulfonate, as pale yellow crystals having a melting point of greater than 280° C. Nuclear magnetic resonance spectroscopy confirmed the structure.

EXAMPLE 4

4-(((4-Bromophenyl)methyl)amino)benzenesulfonic Acid

A mixture of 27.7 g (0.16 mole) of sulfanilic acid, about 28 grams of 50% sodium hydroxide solution, approximately 400 ml of water and 50 grams (0.20 mole) of 4-bromobenzyl bromide were stirred and heated to about 80°–85° C. for 5 hours (hrs). Upon cooling to room temperature, a solid formed which was removed by vacuum filtration. The solid was added to water and the resulting mixture heated and then acidified with concentrated hydrochloric acid. The mixture was filtered while still warm, about 50° C., and the white amorphous solid remaining was air-dried to give 14.8 g of the purified product, 4-(((4-bromophenyl)methyl)amino)benzenesulfonic acid, as a white powder having a melting point greater than 260° C.

An infrared spectrum (potassium bromide pellet) showed broad stretching from 3150–2300 cm$^{-1}$, and intense signals at 1620, 1590, 1435, 1240, 1155, 1120, 1035, 1010, 825 and 680 cm$^{-1}$. A nuclear magnetic resonance spectrum (dimethylsulfoxide-d$_6$ solution) was as follows: δ 9.82 (S, 2H, NH and SO$_3$H), 7.65–7.25 (m, 6H, aromatic), 6.85 (d, J=8 Hz, 2H, aromatic), 4.40 (S, 2H, CH$_2$).

EXAMPLE 5

4-(((4-Chlorophenyl)methyl)amino)benzenesulfonic Acid

To a stirred mixture of 76.6 g (0.44 mole) of sulfanilic acid in 300 ml of water was added 75 g (0.93 mole) of 50% sodium hydroxide solution. The mixture was heated to 80° C. and 100 g (0.62 mole) of 4-chlorobenzyl chloride was added. The dark mixture was stirred at about 80°–85° C. for 4 hours.

After the reaction mixture cooled overnight, the excess 4-chlorobenzyl chloride was removed from the reaction mixture by extracting with diethyl ether. Acidificaton with approximately 40 ml of concentrated hydrochloric acid resulted in the precipitation of a fine tan solid which was removed by filtration. A portion of the solid was recrystallized from 95% ethanol to yield the purified product, 4-(((4-chlorophenyl)methyl)amino)benzenesulfonic acid, having a melting point greater than 270° C.

EXAMPLE 6

4-(((2-Fluorophenyl)methyl)amino)benzenesulfonic Acid

To a mixture of 42.8 g (0.247 mole) of sulfanilic acid in 200 ml of water was added 20 g (0.25 mole) of 50% sodium hydroxide solution. To the resulting dark solution, 50 g (0.345 mole) of 2-fluorobenzyl chloride was added. The mixture was stirred and heated to about 80° C. for 3¾ hours. The reaction mixture was cooled to 50° C. and then vacuum filtered which resulted in the recovery of a light green powder. The powder was stirred in 700 ml of hot water and the mixture was acidified with concentrated hydrochloric acid and then cooled to 40° C. and vacuum filtered leaving 37.7 grams of solid.

A portio of the solid, 28 g, was mixed with ethanol and 50% sodium hydroxide added, utilizing the methodology previously described herein to obtain the sodium salt, sodium-4-(((2-fluorophenyl)methyl)amino)-benzenesulfonate having a melting point of greater than 275° C.

The remaining 9.7 g of solid was recrystallized to give the purified product 4-(((2-fluorophenyl)methyl)amino)benzenesulfonic acid, having a melting point greater than 270° C.

Other subject compounds prepared essentially as described herein are:

EXAMPLE 7

4-(((4-Methylphenyl)methyl)amino)benzenesulfonic Acid, melting point greater than 270° C.

EXAMPLE 8

4-(((2,6-Dichlorophenyl)methyl)amino)benzenesulfonic Acid, melting point greater than 270° C.

EXAMPLE 9

4-(((3,4-Dichlorophenyl)methyl)amino)benzenesulfonic Acid, decomposition at 280° C.

EXAMPLE 10

4-(((3-Fluorophenyl)methyl)amino)benzenesulfonic Acid, melting point greater than 275° C.

EXAMPLE 11

4-(((4-Nitrophenyl)methyl)amino)benzenesulfonic Acid, melting point greater than 275° C.

EXAMPLE 12

4-(((3-(Trifluoromethyl)phenyl)methyl)amino)benzenesulfonic Acid, melting point greater than 275° C.

EXAMPLE 13

4-(((3-Nitrophenyl)methyl)amino)benzenesulfonic Acid, melting point greater than 275° C.

EXAMPLE 14

4-(((2,5-Dimethylphenyl)methyl)amino)benzenesulfonic Acid, melting point greater than 275° C.

EXAMPLE 15

4-(((2,4,6-Trimethylphenyl)methyl)amino)benzenesulfonic Acid, melting point greater than 275° C.

EXAMPLE 16

4-(((3-Bromophenyl)methyl)amino)benzenesulfonic Acid, melting point greater than 275° C.

EXAMPLE 17

4-(((4-(1-Methylethyl)phenyl)methyl)amino)benzenesulfonic Acid

To a 1-liter (1) 3-necked round-bottomed flask equipped with an overhead stirrer, reflux condenser and dropping funnel and containing a stirred mixture of 52.0 g (0.30 mole) of sulfanilic acid in 225 ml of warm (~65° C.) water was added 83.0 g (0.61 mole) of sodium acetate trihydrate and 75 ml of acetonitrile. The temperature of the resulting yellow solution was stabilized at about 70° C. and a solution of 33.8 g (0.20 mole) of 4-(1-methylethyl)benzyl chloride in 75 ml of acetonitrile was added over 70 minutes. The solution was then refluxed for an additional 3½ hrs, and 95 ml of acetonitrile was removed by distillation over a 30 minute period, during which time 50 ml of concentrated hydrochloric acid (con. HCl) was added dropwise. The resulting mixture was filtered hot (~80° C.) and the collected solids were slurried in 300 ml of boiling methanol for 15 min. and then vacuum filtered. The slurrying and vacuum filtration process was repeated first with 300 ml of warm (65° C.) water and then again with 300 ml of boiling methanol. Air-drying of the collected solids gave 12.51 g (20.5% yield) of purified 4-(((4-(1-methylethyl)phenyl)methyl)amino)benzenesulfonic acid as a white powder, having a melting point greater than 275° C.

EXAMPLE 18

4-(((2,4-Dichlorophenyl)methyl)amino)benzenesulfonic Acid

To a mixture of 52.0 g (0.30 mole) of sulfanilic acid in 225 ml of warm water was added 83 g (0.61 mole) of sodium acetate trihydrate and 75 ml of acetonitrile. Then a solution of 37.1 g (0.19 mole) of 2,4-dichlorobenzyl chloride in 75 ml of acetonitrile was added and the resulting solution refluxed for 3½ hrs, followed by the dropwise addition of 50 ml of conc. HCl while simultaneously removing 75 ml of acetonitrile by distillation. The reaction mixture was filtered while hot (80° C.) and the same purification sequence utilized as described in the previous example, which gave 34.91 g (55.3% yield) of purified 4-(((2,4-dichlorophenyl)methyl)amino)benzenesulfonic acid as a white powder having a melting point greater than 275° C.

EXAMPLE 19

4-(((4-Benzoylphenyl)methyl)amino)benzenesulfonic Acid

To a stirred melt of 75.0 g (0.38 mole) of 4-methylbenzophenone maintained at a temperature of approximately 150° C. in a 500-ml 3-necked round-bottomed flask equipped with overhead stirrer, reflux condenser and dropping funnel was added 61 g (19.7 ml, 0.38 mole) of bromine. The dark mixture was stirred at 150° C. for an additional hour and then allowed to cool to about 90° C. The mixture was then poured into water, resulting in the formation of an oil which solidified upon standing overnight, affording about 70 g of a cream-colored solid. The cream-colored solid was recrystallized from absolute ethanol to give 42.6 g of tan needles, mp 81°–85° C. A second recrystallization from 95% ethanol afforded 36.3 g of purified 4-(bromomethyl)benzophenone as tan flakes, mp 85°–89° C.

To a 1-liter 3-necked round-bottomed flask equipped with overhead stirrer, reflux condenser, dropping funnel and thermometer and containing a stirred slurry of 33.8 g (0.195 mole) of sulfanilic acid in 150 ml of warm (60° C.) water was added 55 g (0.404 mole) of sodium acetate trihydrate and 50 ml of acetonitrile. The resulting yellow solution was heated to 70° C. and a solution of 35 g (0.127 mole) of the 4-(bromomethyl)benzophenone prepared above in 80 ml of acetonitrile was added dropwise over 1½ hrs. The resulting solution was then refluxed for 5 hrs. Approximately 75 ml of acetonitrile was then removed by distillation at the same time that a dropwise addition of 32 ml of conc. HCl (over a 20 minute period) was made. The mixture was then vacuum filtered at 80° C. which gave a pale yellow powder. The powder was then slurried in 250 ml of water for 15 minutes and again isolated by vacuum filtration. The resulting solids were reslurried in 250 ml of methanol and isolated by vacuum filtration which afforded 25.28 g (54.2%) of purified 4-(((4-benzoylphenyl)methyl)amino)benzenesulfonic acid as a pale yellow powder, which decomposed at 257°–259° C.

EXAMPLE 20

4-(((-4-(Methylsulfonyl)phenyl)methyl)amino)benzenesulfonic Acid, melting point greater than 260° C.

The compound of example 20 was prepared essentially as described in the preceding examples.

EXAMPLE 21

3-(((3,4-Dichlorophenyl)methyl)amino)benzenesulfonic Acid

To a warm (~65° C.) mixture of 52.0 g (0.30 mole) of 3-aminobenzenesulfonic acid in 225 ml of water was added 50.3 g (0.61 mole) of sodium acetate, and 75 ml of acetonitrile. The resulting dark solution was warmed to approximately 70° C., and a solution of 39.1 g (0.20 mole) of 3,4-dichlorobenzyl chloride in 75 ml of acetonitrile was added dropwise over 55 minutes. The dark solution was then heated at reflux for 2½ hrs. To this solution was then added 48 ml of conc. HCl dropwise over 30 minutes at the same time that 85 ml of acetonitrile was removed by distillation.

The resulting mixture was vacuum filtered at 80° C. and air-dried to give 53.14 g of off-white powder. The powder was slurried in 200 ml of water at 80° C. for 20 minutes, and then isolated by vacuum filtration. The resulting solids were reslurried in 200 ml of boiling methanol for 20 minutes, and then isolated by vacuum filtration. The solids were then dried overnight in vacuo at 50° C. which afforded 36.2 g (54.8%) of purified 3-(((3,4-dichlorophenyl)methyl)amino)benzenesulfonic acid as a white powder having a melting point greater than 275° C.

EXAMPLE 22

3-(((3-(Trifluoromethyl)phenyl)methyl)amino)benzenesulfonic Acid

To 52.0 g (0.30 mole) of 3-aminobenzenesulfonic acid in 225 ml of water was added 83.0 g (0.61 mole) of sodium acetate trihydrate and 75 ml of acetonitrile. The solution was stabilized at about 70° C. and a solution of 38.92 g (0.20mole) of 3-(trifluoromethyl)benzyl chloride in 75 ml of acetonitrile was added dropwise. The resulting orange solution was refluxed for 4 hrs, then acidified by the dropwise addition of 42 ml of conc. HCl while simultaneously removing 105 ml of acetonitrile by distillation. After standing overnight, a flocculent cream-colored solid crystalized which was removed by vacuum filtration. The collected solids were then slurried in 300 ml of warm (60° C.) water for 20 minutes and then filtered. The slurrying process was repeated using 300 ml of boiling methanol and the solids isolated by vacuum filtration. Air-drying in vacuo at about 60° C. gave 15.4 g (23.2% yield) of purified 3-(((3-(trifluoromethyl)phenyl)methyl)amino)benzenesulfonic acid as a white powder having a melting point greater than 275° C.

EXAMPLE 23

3-(((4-Nitrophenyl)methyl)amino)benzenesulfonic Acid

After 52.0 g (0.30 mole) of 3-aminobenzenesulfonic acid in 225 ml of warm (65° C.) water and 83.0 (0.61 mole) of sodium acetate trihydrate in 75 ml of acetonitrile was combined and the temperature stabilized at approximately 68°–70° C., 43.2 g (0.20 mole) of 4-nitrobenzyl bromide in 85 ml of warmed acetonitrile was added dropwise over 70 minutes. The orange-red solution was then refluxed for 2 hrs, then acidified with 42 ml of conc. HCl over 40 minutes while simultaneously distilling off 110 ml of acetonitrile. The mixture was filtered hot (70° C.) which gave a light yellow powder. The powder was slurried in 275 ml of hot (75° C.) water for 20 minutes and then filtered. The slurrying process was repeated with water and then with methanol which gave a cream-colored powder. The cream-colored powder was dried in vacuo overnight at 50° C. to afford 35.33 g (57.3% yield) of purified 3-(((4-nitrophenyl)methyl)amino)benzenesulfonic acid as a cream-colored powder having a melting point greater than 275° C.

EXAMPLE 24

3-(((2,5-Dimethylphenyl)methyl)amino)benzenesulfonic Acid

To a stirred slurry of 52.0 g (0.30 mole) of 3-aminobenzenesulfonic acid in 225 ml of hot (65° C.) water was added 83.0 g (0.61 mole) of sodium acetate trihydrate and 75 ml of acetonitrile. The temperature was stabilized at approximately 67°–68° C. and a solution of 30.93 g (0.20 mole) of 2,5-dimethylbenzyl chloride in 75 ml of acetonitrile added dropwise over 1 hr. The resulting orange solution was refluxed for 3½ hrs, then acidified with 40 ml of conc. HCl while simultaneously distilling off 80 ml of acetonitrile. After placing the reaction mixture in a refrigerator a flocculent cream-colored precipitate formed which was collected by vacuum filtration, washed with water and air-dried. The collected solids were then slurried in 400 ml of boiling methanol for 20 minutes, then vacuum filtered and then dried in vacuo at about 60° C., which afforded 30.86 g (53.0% yield) of purified 3-(((2,5-dimethylphenyl)methyl)amino)benzenesulfonic acid as a white powder having a melting point greater than 275° C.

EXAMPLE 25

3-(((2,4,6-Trimethylphenyl)methyl)amino)benzenesulfonic Acid

A mixture of 52.0 g (0.30 mole) of 3-aminobenzenesulfonic acid, 83.0 g (0.61 mole) of sodium acetate trihydrate, 33.7 g (0.20 mole) of 2,4,6-trimethylbenzyl chloride, 225 ml of water and 150 ml of acetonitrile was refluxed for 4 hrs, then acidified by the dropwise addition of 40 ml of conc. HCl over 30 minutes during which time approximately 100 ml of acetonitrile was distilled off. The resulting mixture was vacuum filtered while hot (80° C.) and a grayish-white powder obtained which was then slurried in 300 ml of hot (65° C.) water for 20 minutes and vacuum filtered. The slurrying process was repeated with water and then with 300 ml of boiling methanol for 20 minutes. Vacuum filtration followed by drying in vacuo at about 60° C. afforded 24.85 g (40.7% yield) of purified 3-(((2,4,6-trimethylphenyl)methyl)amino)benzenesulfonic acid as a white powder having a melting point greater than 275° C.

Other subject compounds prepared essentially as described herein are:

EXAMPLE 26

3-(((3-Bromophenyl)methyl)amino)benzenesulfonic Acid, melting point greater than 275° C.

EXAMPLE 27

3-(((3-Chlorophenyl)methyl)amino)benzenesulfonic Acid, melting point greater than 275° C.

EXAMPLE 28

3-(((4-Chlorophenyl)methyl)amino)benzenesulfonic Acid, melting point greater than 285° C.

EXAMPLE 29

3-(((2,6-Dichlorophenyl)methyl)amino)benzenesulfonic Acid, melting point greater than 275° C.

EXAMPLE 30

3-(((3-Nitrophenyl)methyl)amino)benzenesulfonic Acid, melting point greater than 275° C.

EXAMPLE 31

3-(((4-Methylphenyl)methyl)amino)benzenesulfonic Acid, melting point greater than 285° C.

EXAMPLE 32

3-(((2,4-Dimethylphenyl)methyl)amino)benzenesulfonic Acid, melting point greater than 275° C.

EXAMPLE 33

3-(((4-Fluorophenyl)methyl)amino)benzenesulfonic Acid, melting point greater than 285° C.

EXAMPLE 34

3-(((4-Bromophenyl)methyl)amino)benzenesulfonic Acid, melting point greater than 285° C.

EXAMPLE 35

3-(((2-Chlorophenyl)methyl)amino)benzenesulfonic Acid, melting point greater than 275° C.

EXAMPLE 36

3-(((4-(1-Methylethyl)phenyl)methyl)amino)benzenesulfonic Acid, melting point greater than 275° C.

The physical properties of the above examples are summarized in Table 1.

TABLE 1

| Compound Example Number | % Yield | mp, °C. | Calculated % | | | Found % | | |
|---|---|---|---|---|---|---|---|---|
| | | | C | H | N | C | H | N |
| 1 | 17.5 | >280 | 48.84 | 3.47 | 4.38 | 48.8 | 3.58 | 4.57 |
| 2 | 29.7 | 275 decomp. | 51.49 | 3.66 | 4.62 | 51.5 | 3.71 | 4.81 |
| 3 | 21.9 | >280 | * | | | | | |
| 4 | 22.4 | >260 | 45.62 | 3.54 | 4.09 | 45.64 | 3.65 | 3.95 |
| 5 | 1.1 | >270 | 52.43 | 4.06 | 4.70 | 52.71 | 4.10 | 4.68 |
| 6 | 34.1 | >270 | 55.50 | 4.30 | 4.98 | 55.3 | 4.35 | 5.05 |
| 7 | 11.5 | >270 | 60.63 | 5.45 | 5.05 | 60.35 | 5.77 | 5.16 |
| 8 | 33.6 | >270 | 47.00 | 3.34 | 4.22 | 46.75 | 3.59 | 4.19 |
| 9 | 63.3 | 280 decomp. | 47.00 | 3.34 | 4.22 | 46.83 | 3.32 | 4.20 |
| 10 | 13.4 | >275 | 55.50 | 4.30 | 4.98 | 55.38 | 4.41 | 5.02 |
| 11 | 73.4 | >275 | 50.64 | 3.92 | 9.09 | 50.34 | 3.91 | 8.84 |
| 12 | 57.3 | >275 | 50.75 | 3.65 | 4.23 | 50.57 | 3.81 | 4.45 |
| 13 | 30.8 | >275 | 50.64 | 3.92 | 9.09 | 50.34 | 4.11 | 9.07 |
| 14 | 59.4 | >275 | 61.83 | 5.88 | 4.81 | 61.62 | 5.72 | 4.67 |
| 15 | 43.6 | >275 | 62.92 | 6.27 | 4.59 | 62.67 | 6.38 | 4.29 |
| 16 | 61.4 | >275 | 45.62 | 3.54 | 4.09 | 45.53 | 3.47 | 4.14 |
| 17 | 20.5 | >275 | 62.92 | 6.27 | 4.59 | 63.23 | 6.34 | 4.79 |
| 18 | 55.3 | >275 | 47.00 | 3.34 | 4.22 | 46.73 | 3.46 | 4.20 |
| 19 | 54.2 | 257–259 decomp. | 65.37 | 4.66 | 3.81 | 65.64 | 4.57 | 3.80 |
| 20 | 62.1 | >260 | 49.25 | 4.43 | 4.10 | 49.49 | 4.30 | 3.98 |
| 21 | 54.8 | >275 | 47.00 | 3.34 | 4.22 | 46.77 | 3.45 | 4.18 |
| 22 | 23.2 | >275 | 50.75 | 3.65 | 4.23 | 50.95 | 3.78 | 4.27 |
| 23 | 57.3 | >275 | 50.64 | 3.92 | 9.09 | 50.37 | 3.93 | 8.85 |
| 24 | 53.0 | >275 | * | | | | | |
| 25 | 40.7 | >275 | 62.92 | 6.27 | 4.59 | 63.15 | 6.37 | 4.39 |
| 26 | 53.1 | >275 | 45.62 | 3.54 | 4.09 | 45.53 | 3.47 | 4.14 |
| 27 | 35.8 | >275 | 52.43 | 4.06 | 4.70 | 52.17 | 4.09 | 4.80 |
| 28 | 48.3 | >285 | * | | | | | |
| 29 | 63.5 | >275 | 47.00 | 3.34 | 4.22 | 47.19 | 3.30 | 4.17 |
| 30 | 62.3 | >275 | 50.64 | 3.92 | 9.09 | 50.36 | 4.04 | 8.86 |
| 31 | 13.2 | >285 | 60.63 | 5.45 | 5.05 | 60.36 | 5.31 | 5.33 |
| 32 | 25.1 | >275 | 61.83 | 5.88 | 4.81 | 61.59 | 5.72 | 4.51 |
| 33 | 30.3 | >285 | 55.50 | 4.30 | 4.98 | 55.29 | 4.32 | 5.15 |
| 34 | 37.8 | >285 | 45.62 | 3.54 | 4.09 | 45.52 | 3.60 | 3.98 |
| 35 | 43.9 | >275 | 52.43 | 4.06 | 4.70 | 52.68 | 4.13 | 4.69 |
| 36 | 20.5 | >275 | 62.92 | 6.27 | 4.59 | 63.23 | 6.34 | 4.79 |

*The structure of the indicated test compound was confirmed by infrared spectroscopy and/or nuclear magnetic resonance spectroscopy.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture media such as those described herein are more fully described in standard texts, as for example, Kuchler's Biochemical Methods in Cell Culture and Virology, Dowden, Hutchinson and Ross, Inc., Stroudsberg, PA. (1977). Following treatment, cells were challenged with 0.05 ml of rhinovirus type 1A (RV-1A), rhinovirus type 2 (RV-2) or Coxsackie $A_{21}$ virus (Cox $A_{21}$) in culture medium. Some of the compounds were also tested against rhinovirus type 5 (RV-5), rhinovirus type 8 (RV-8) or rhinovirus type 64 (RV-64). Cell controls received no viruses. Cultures were observed for compound cytotoxicity and viral cytopathic effect (CPE) at 48 and 72 hours post-treatment.

Some of the subject compounds were also tested in animals as follows:

Swiss male mice, 10–12 grams in weight, were challenged intraperitonially (IP) with 0.2 ml of a normally lethal dose, i.e. a virus dose sufficient to cause ≅80–100% mortality in infected animals within 10 days of challenge of Cox $A_{21}$ virus in phosphate buffered saline containing heat inactivated fetal calf serum. Three hours later mice were treated IP or orally (PO) with 0.2 ml of compound suspended in 0.5% hydroxypropyl methylcellulose (Methocel) or with 0.2 ml of Methocel alone. Compound suspensions had a concentration of 7.5 milligrams/milliliter (mg/ml) which as administered to the animal was equivalent to a dosage of 150 milligrams/kilogram (mg/kg); 20 mg/ml (400 mg/kg); or 30 mg/ml (600 mg/kg). Mice were observed daily for 7–10 days post-challenge and deaths recorded. A modified Mantel-Haenzel combined chi-square ($\chi^2$) procedure was used to determine significant difference between virus control and treated groups. Chi-square values greater than 3.84 and considered significant (95% confidence level) in this test.

Results obtained from the above-noted testing are summarized in Table 2.

TABLE 2

| Compound Example Number | Cytotoxicity* ($\mu$g/ml) | Tissue Culture Testing** | | | | | | Animal Testing | | | |
|---|---|---|---|---|---|---|---|---|---|---|---|
| | | | | | | | | ip | | po | |
| | | RV-1A | RV-2 | Cox $A_{21}$ | RV-5 | RV-8 | RV-64 | Dose (mg/kg) | $\chi^2$ | Dose (mg/kg) | $\chi^2$ |
| 1 | >200 | 1.25 | 25 | 25 | | | | 400 | 11.049 | 600 | 4.8 |
| 2 | >200 | 1.25 | 200 | 50 | | | | 400 | 21.467 | 600 | 13.2 |
| 3 | >200 | 1.25 | 100 | 25 | | | | 150 | 1.086 | | |
| 4 | >100 | <6.25 | ≦12.5 | ≦12.5 | | | | | | 600 | 0.201 |
| 5 | >100 | 0.156 | 50 | <6.25 | | | | | | 600 | 5.34 |
| 6 | >100 | ≦6.25 | NA | NA | | | | | | 600 | 1.133 |
| 7 | >100 | <6.25 | 25 | 25 | | | | | | 600 | 1.31 |
| 8 | ≧100 | NA | NA | 100 | | | | | | 600 | 0.29 |
| 9 | >100 | <6.25 | ≦6.25 | 12.5 | 25 | NA | <6.25 | | | 600 | 0.264 |
| 10 | >100 | <6.25 | NA | NA | | | | | | 600 | 5.22 |
| 11 | >100 | <<6.25 | 6.25 | 6.25 | NA | NA | <6.25 | | | | |
| 12 | >100 | <6.25 | 6.25 | 50 | NA | NA | <<6.25 | | | | |
| 13 | >100 | <6.25 | 50 | <6.25 | NA | NA | 12.5 | | | | |
| 14 | >100 | <6.25 | NA | 100 | | | | | | | |
| 15 | 100 | <6.25 | NA | 50 | | | | | | | |
| 16 | >100 | <<6.25 | 25 | 50 | | | | | | | |
| 17 | >100 | 12.5 | 25 | NA | | | | | | | |
| 18 | >100 | <6.25 | 50 | 100 | | | | | | | |
| 19 | >100 | <<6 | 6 | 100 | | | | | | | |
| 20 | >400 | 200 | NA | | | | NA | | | | |
| 21 | >100 | <6.25 | 12.5 | 25 | 25 | NA | 6.25 | | | 600 | ***9.63 toxic |
| 22 | >100 | <6.25 | 50 | 100 | | | | | | | |
| 23 | >100 | <6.25 | 12.5 | ±100 | | | | | | | |
| 24 | >100 | <6.25 | ±100 | 100 | | | | | | | |
| 25 | 50 | <<6.25 | 12.5 | 25 | | | | | | 600 | 0.007 |
| 26 | >100 | <<6.25 | 100 | 50 | | | | | | 600 | 0.004 |
| 27 | >100 | <6.25 | 50 | NA | | | | | | | |
| 28 | >100 | <6.25 | ≦6.25 | NA | NA | NA | 12.5 | | | 600 | ***12.029 toxic |
| 29 | >100 | ≦6.25 | 100 | NA | | | | | | | |
| 30 | >100 | ≦6.25 | NA | NA | | | | | | 600 | 0.110 |
| 31 | >100 | <6.25 | ≦6.25 | 100 | 6.25 | NA | 12.5 | | | 600 | 0.108 |
| 32 | >100 | <<6.25 | 12.5 | >100 | | | | | | 600 | 0.123 |
| 33 | >100 | <6.25 | 25 | NA | | | | | | | |
| 34 | >100 | <6.25 | <6.25 | 100 | 100 | NA | 6.25 | | | 600 | 0.209 |
| 35 | >100 | <6.25 | 50 | NA | | | | | | | |
| 36 | >100 | ±100 | 100 | NA | | | | | | | |

*Cytotoxicity figures represent the concentration of the compound, micrograms/milliliter ($\mu$g/ml) found to be toxic to the cell.
**Lowest concentration of the compound ($\mu$g/ml) necessary to cause a 50 percent reduction in cytopathic effect.
***The test compound was significantly toxic at the indicated dosage.
The symbol "NA" indicates that the compound was not active against that particular virus at the standard test conditions; "<" means "less than"; "≦" means "less than or equal to"; ">" means "greater than"; "≧" means "greater than or equal to"; "±" means "approximately"; and "<<" means "considerably less than".

The data in Table 2 demonstrate the antiviral activity of representative compounds falling within the scope of the present invention.

The test data indicate that all of the tested compounds are active against at least one of the test viruses, (RV-1A, RV-2, RV-5, RV-8, RV-64 or Cox $A_{21}$). In additon, several of the subject compounds (at the 95% confidence level) are active antiviral compounds in testing with mice. When tested in another tissue culture testing system, the compound 4-(((4-bromophenyl)meythyl)amino)benzenesulfonic acid (Example 4) inhibited fifteen of the twenty rhinovirus types it was tested against when the compound was used at a 100 $\mu$g/ml concentration. Because of their demonstrated antiviral activity compounds of the formula

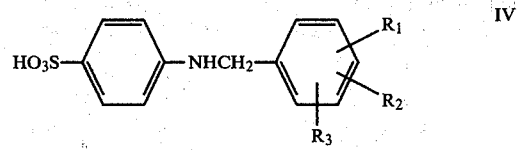

or a pharmaceutically-acceptable salt thereof wherein R₁ represents halogen; R₂ represents halogen or hydrogen; and R₃ represents hydrogen are preferred.

In using the compounds of the invention, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner which ensures continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an antiviral dosage of a compound of the invention to an animal (preferably a mammal). The compounds can be administered to animals parenterally (for example, by intraperitoneal, subcutaneous or intravenous injection) or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, such as, for example, the 0.156 μg/ml of 4-(((4-chlorophenyl)methyl)amino)benzenesulfonic acid (Example 5) which caused a 50% reduction in cytopathic effect in testing against test virus RV-1A.

Such compositions can contain from about 0.1 microgram or less of the active compound per milliliter of carrier to about 99 percent by weight of the active compound in combination with a pharmaceutically-acceptable carrier.

Preferred compositions include compositions containing from about 0.1 μg of active compound per milliliter of carrier to about 0.0025 to about 0.05 to about 0.25 to about 0.5 to about one to about 10 to about 25 to about 50 percent by weight of active compound in a pharmaceutically-acceptable carrier.

The compositions can be in solid forms such as tablets, capsules, granulations, feed mixes, feed supplements and concentrates, powders, granules or the like; as well as liquid forms such as sterile injectable suspensions, orally administered suspensions, or solutions. The pharmaceutically-acceptable carriers can include excipients, such as surface active dispersing agents, suspending agents, tableting binders, lubricants, flavors and colorants. Suitable excipients are disclosed, for example, in texts such as Remington's Pharmaceutical Manufacturing Thirteenth Edition, Mack Publishing Co., Easton, PA. (1965).

What is claimed is:

1. A compound of the formula:

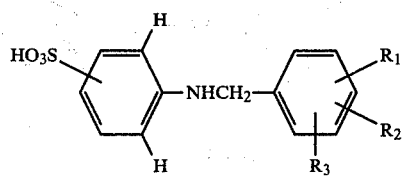

or a pharmaceutically-acceptable salt thereof wherein R₁ represents lower alkyl, lower alkoxy, amino, cyano, trifluoromethyl, acetyl, methylthio, methylsulfinyl, methylsulfonyl, benzoyl, substituted benzoyl or aminosulfonyl; and R₂ and R₃ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl or aminosulfonyl.

2. The compound of claim 1 which is 4-(((3,4-dimethylphenyl)methyl)amino)benzenesulfonic acid or a pharmaceutically-acceptable salt thereof.

3. The compound of claim 1 which is 4-(((4-methylphenyl)methyl)amino)benzenesulfonic acid or a pharmaceutically-acceptable salt thereof.

4. The compound of claim 1 which is 4-(((3-(trifluoromethyl)phenyl)methyl)amino)benzenesulfonic acid or a pharmaceutically-acceptable salt thereof.

5. The compound of claim 1 which is 4-(((2,5-dimethylphenyl)methyl)amino)benzenesulfonic acid or a pharmaceutically-acceptable salt thereof.

6. The compound of claim 1 which is 4-(((2,4,6-trimethylphenyl)methyl)amino)benzenesulfonic acid or a pharmaceutically-acceptable salt thereof.

7. The compound of claim 1 which is 4-(((4-(1-methylethyl)phenyl)methyl)amino)benzenesulfonic acid or a pharmaceutically-acceptable salt thereof.

8. The compound of claim 1 which is 4-(((4-benzoylphenyl)methyl)amino)benzenesulfonic acid or a pharmaceutically-acceptable salt thereof.

9. The compound of claim 1 which is 4-(((4-(methylsulfonyl)phenyl)methyl)amino)benzenesulfonic acid or a pharmaceutically-acceptable salt thereof.

10. The compound of claim 1 which is 3-(((3-(trifluoromethyl)phenyl)methyl)amino)benzenesulfonic acid or a pharmaceutically-acceptable salt thereof.

11. The compound of claim 1 which is 3-(((2,5-dimethylphenyl)methyl)amino)benzenesulfonic acid or a pharmaceutically-acceptable salt thereof.

12. The compound of claim 1 which is 3-(((2,4,6-trimethylphenyl)methyl)amino)benzenesulfonic acid or a pharmaceutically-acceptable salt thereof.

13. The compound of claim 1 which is 3-(((4-methylphenyl)methyl)amino)benzenesulfonic acid or a pharmaceutically-acceptable salt thereof.

14. The compound of claim 1 which is 3-(((2,4-dimethylphenyl)methyl)amino)benzenesulfonic acid or a pharmaceutically-acceptable salt thereof.

15. The compound of claim 1 which is 3-(((4-(1-methylethyl)phenyl)methyl)amio)benzenesulfonic acid or a pharmaceutically-acceptable salt thereof.

16. A method for inhibiting viruses which comprises contacting viruses or virus host cells with an effective virus inhibiting amount of a compound represented by the formula:

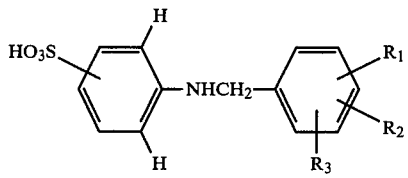

or a pharmaceutically-acceptable salt thereof wherein $R_1$ represents lower alkyl, lower alkoxy, nitro, amino, cyano, trifluoromethyl, acetyl, methylthio, methylsulfinyl, methylsulfonyl, benzoyl, substituted benzoyl, aminosulfonyl or halogen; and $R_2$ and $R_3$ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl, aminosulfonyl or halogen.

17. A method for inhibiting viruses which comprises administering to an animal an effective virus inhibiting amount of a compound represented by the formula:

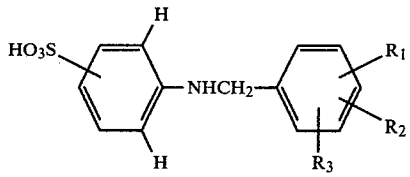

or a pharmaceutically-acceptable salt thereof wherein $R_1$ represents lower alkyl, lower alkoxy, nitro, amino, cyano, trifluoromethyl, acetyl, methylthio, methylsufinyl, methylsulfonyl, benzoyl, substituted benzoyl, aminosulfonyl or halogen; and $R_2$ and $R_3$ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl, aminosulfonyl or halogen.

18. A composition for inhibiting viruses comprising a pharmaceutically-acceptable carrier in combination with an effective virus inhibiting amount of a compound represented by the formula:

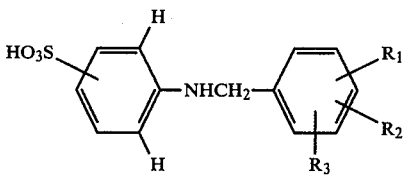

or a pharmaceutically-acceptable salt thereof wherein $R_1$ represents lower alkyl, lower alkoxy, amino, cyano, trifluoromethyl, acetyl, methylthio, methylsulfinyl, methylsulfonyl, benzoyl, substituted benzoyl or aminosulfonyl; and $R_2$ and $R_3$ are the same or different and are selected from the group consisting of hydrogen, lower alkyl, lower alkoxy, amino, cyano, trifluoromethyl, acetyl, methylthio, methylsulfinyl, methylsulfonyl, benzoyl, substituted benzoyl or aminosulfonyl.

* * * * *

UNITED STATES PATENT AND TRADEMARK OFFICE
CERTIFICATE OF CORRECTION

PATENT NO. : 4,328,244
DATED : May 4, 1982
INVENTOR(S) : John K. Daniel, et al.

It is certified that error appears in the above—identified patent and that said Letters Patent is hereby corrected as shown below:

Column 5, line 12, "sodium-4-" should read -- sodium 4- --.

Column 10, Table 1, under subheading % Yield, Example Number 13, "30.8" should read --80.6--.

Signed and Sealed this

Seventh Day of September 1982

[SEAL]

Attest:

GERALD J. MOSSINGHOFF

*Attesting Officer*  *Commissioner of Patents and Trademarks*